United States Patent [19]

Biedermann et al.

[11] Patent Number: 5,742,395
[45] Date of Patent: Apr. 21, 1998

[54] METHOD FOR CHECKING SEMICONDUCTOR WAFERS AND APPARATUSES FOR CARRYING OUT THE METHOD

[75] Inventors: Ernst Biedermann, Regensburg; Matthias Grieshop, Neutraubling; Manfred Ben El Mekki, Fürstenfeldbruck; Kenneth Weisheit, Augsburg; Thomas Griebsch; Gerhard Ross, both of München, all of Germany

[73] Assignee: Siemens Aktiengesellschaft, Munich, Germany

[21] Appl. No.: 425,827

[22] Filed: Apr. 20, 1995

[30] Foreign Application Priority Data

Apr. 20, 1994 [DE] Germany .................. 44 13 831.8

[51] Int. Cl.⁶ ............................................... G01B 11/00
[52] U.S. Cl. ........................................ 356/394; 356/237
[58] Field of Search .......................... 356/394, 237, 356/239, 371, 354, 347; 348/126; 382/149, 147, 148, 145, 153

[56] References Cited

U.S. PATENT DOCUMENTS 4,740,708  4/1988  Batchelder .................. 356/237
4,929,081  5/1990  Yamamoto et al. ........... 356/354

FOREIGN PATENT DOCUMENTS

| 0 159 354 | 4/1987 | European Pat. Off. . |
| 38 06 209 | 9/1988 | Germany . |
| 40 03 983 | 8/1991 | Germany . |
| 40 32 327 | 7/1992 | Germany . |

Primary Examiner—Hoa Q. Pham
Attorney, Agent, or Firm—Herbert L. Lerner; Laurence A. Greenberg

[57] ABSTRACT

In a method for checking semiconductor wafers and apparatuses for carrying out the method, a lacquer layer applied on a semiconductor wafer is checked. Initially, regions which are to be excluded from the check and surfaces which are to be checked, are ascertained. The checking is effected by direct illumination in such a way that the lacquer layer reflects light. The resulting values of the reflectance are determined and buffer-stored. A determination is performed for each surface as to whether or not it is to be accepted or rejected, in accordance with a predetermined evaluation criterion.

16 Claims, 3 Drawing Sheets

METHOD FOR CHECKING SEMICONDUCTOR WAFERS AND APPARATUSES FOR CARRYING OUT THE METHOD

BACKGROUND OF THE INVENTION

FIELD OF THE INVENTION

The invention relates to a method for checking semiconductor wafers, especially a batch of semiconductor wafers, and apparatuses for carrying out the method.

A batch of semiconductor wafers is known to include a plurality of semiconductor wafers, which are a component of a single production lot. The semiconductor wafers to be checked already have at least one first layer with structures, as well as a lacquer layer as a top layer. The semiconductor wafers are used to manufacture integrated semiconductor memories. In the method, the top layer, that is the lacquer layer, and the semiconductor layers under it, are to be checked for satisfactory characteristics. Defective semiconductor wafers need to be detected in the process, so that they can either be eliminated from the further course of production entirely or be suitably reworked before further production steps are performed on them and they are then returned to the normal course of production, on the condition that they are free of defects.

Checks of semiconductor wafers for perfect characteristics (for instance checking for freedom from particles, or in other words soil and deposits, checking for a uniformly thick lacquer layer or for defects in the lacquer layer) are known to be eminently important if good yields in the production process are to be attained.

Heretofore, such checks have been carried out manually, either with the aid of microscopes or without a microscope, by means of light striking obliquely. On one hand, that is very tiring for the worker, especially for his or her eyes and back (because of posture and long hours of sitting). On the other hand, it involves major uncertainties as well, since the worker's concentration on detecting defects and sorting out good and bad wafers diminishes over time.

SUMMARY OF THE INVENTION

It is accordingly an object of the invention to provide a method for checking semiconductor wafers and apparatuses for carrying out the method, which overcome the hereinafore-mentioned disadvantages of the heretofore-known methods and apparatuses of this general type, which permit the process of checking to be made as error-free as possible and which permit strains on the health of workers to be reduced.

With the foregoing and other objects in view there is provided, in accordance with the invention, in a method for checking semiconductor wafers or a batch of semiconductor wafers used to produce integrated semiconductor memories, in which the semiconductor wafers have a lacquer layer and at least one layer having structures below the lacquer layer, the improvement which comprises automatically:

1) ascertaining regions to be omitted from the check and surfaces to be checked, at least for first semiconductor wafers to be checked, in accordance with the following steps:
   1a) directly illuminating the semiconductor wafer for reflecting light from the applied lacquer layer;
   1b) ascertaining and buffer-storing reflectance of the reflected light with a camera disposed vertically above the semiconductor wafer and an evaluator connected to the camera, in the following way:
      1b1) ascertaining and buffer-storing the reflectance of the reflected light at selected points along two imaginary lines drawn over the semiconductor wafer at right angles to one another, with one of the lines being aimed in a forward direction of the structures;
      1b2) repeating step 1b1) for a further imaginary line being spaced apart from and parallel to the imaginary line and having multiple values below a predetermined minimum value, if multiple values for the reflectance being below the minimum value occur for at least one of the imaginary lines;
      1b3) repeating step 1b2) with further imaginary lines being spaced apart from the last imaginary line measured most recently, if step 1b2) for the further imaginary line also leads to values of the reflectance being below the minimum value multiple times, often enough until an imaginary line is found having values of the reflectance meeting the criterion of the minimum value multiple times;
   1c) discontinuing the check if steps 1b1) through 1b3) do not lead to two imaginary lines at right angles to one another meeting the criterion of the minimum value; otherwise ascertaining coordinates being above a predetermined maximum value but in the vicinity of position values having a reflectance below the maximum value for each of the two imaginary lines, from their position points, from associated values of the reflectance and from information stating that the semiconductor wafer serves to produce integrated semiconductor memories;
   1d) utilizing a quantity of the coordinates thus found in a remainder of the method to eliminate regions of the semiconductor wafer to be checked, from the check, for finding a number of surfaces to be checked for the semiconductor wafer to be checked, having coordinates of corner points being equal to the ascertained respective coordinates;
2) checking each surface during illumination, by the following method steps:
   2a) drawing at least one imaginary measuring line through the surface to be checked;
   2b) ascertaining and buffer-storing a respective value of the reflectance of the reflected light at predetermined measuring points along the measuring line with the camera and the evaluator;
   2c) ascertaining whether the checked surface is OK or defective in accordance with at least one predetermined evaluation criterion, from the ascertained and buffer-stored values of the reflectance; and
   2d) ascertaining surfaces found to be defective.

With the objects of the invention in view, there is also provided an apparatus for automatically checking semiconductor wafers or a batch of semiconductor wafers used to produce integrated semiconductor memories, comprising a receiver for a semiconductor wafer to be checked, the receiver having a center point; a light for directly illuminating the semiconductor wafer; a hemispherical hood having a surface absorbing light striking the hood from inside, the hemispherical hood defining an interior with an interior chamber; a further hood being disposed above the light, being opaque to incident light, and permitting the semiconductor wafer to be illuminated directly by the light; a camera being disposed at the hemispherical hood vertically above the center point of the receiver for the semiconductor wafer to be checked, the camera having a lens looking into the interior chamber of the hemispherical hood; and an evaluator connected to the camera for controlling the camera and for receiving, buffer-storing, processing and outputting data transmitted by the camera.

With the objects of the invention in view, there is additionally provided an apparatus for automatically checking semiconductor wafers or a batch of semiconductor wafers used to produce integrated semiconductor memories, comprising a receiver for a semiconductor wafer to be checked, the receiver having a center point; a light for indirectly illuminating the semiconductor wafer; a hemispherical hood having a surface to a great extent reflecting light striking the hood from inside, the hemispherical hood defining an interior with an interior chamber; a further opaque hood being disposed between the light and the receiver for the semiconductor wafer to be checked, the further opaque hood only permitting the semiconductor wafer to be illuminated indirectly by the light; a camera being disposed at the hemispherical hood and having a lens looking into the interior chamber, the camera CAM being disposed at an angle greater than 0° and less than 90° relative to the center point of the receiver for the semiconductor wafer to be checked; and an evaluator connected to the camera for controlling the camera and for receiving, buffer-storing, processing and outputting data transmitted by the camera.

With the objects of the invention in view, there is furthermore provided an apparatus for automatically checking semiconductor wafers or a batch of semiconductor wafers used to produce integrated semiconductor memories, comprising a receiver for a semiconductor wafer to be checked, the receiver having a center point; a first light for directly illuminating the semiconductor wafer with light of a first color; a second light for indirectly illuminating the semiconductor wafer with light of a second color being complementary to the first color; a hemispherical hood having a surface of the second color, the hemispherical hood defining an interior with an interior chamber; a further hood being disposed above the first light, being opaque to incident light, permitting the semiconductor wafer to be illuminated directly by the first light, and permitting the semiconductor wafer to only be illuminated indirectly by the second light; a first camera being disposed at the hemispherical hood vertically above the center point of the receiver for the semiconductor wafer to be checked, the first camera having a lens looking into the interior chamber and having a filter admitting only light of the first color; a second camera being disposed at the hemispherical hood and having a lens looking into the interior chamber and a filter admitting only light of the second color, the second camera being disposed at an angle greater than 0° relative to the center point of the receiver for the semiconductor wafer to be checked; and an evaluator connected to both of the cameras for controlling the cameras and for receiving, buffer-storing, further processing and outputting data transmitted from the cameras.

Other features which are considered as characteristic for the invention are set forth in the appended claims.

Although the invention is illustrated and described herein as embodied in a method for checking semiconductor wafers and apparatuses for carrying out the method, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
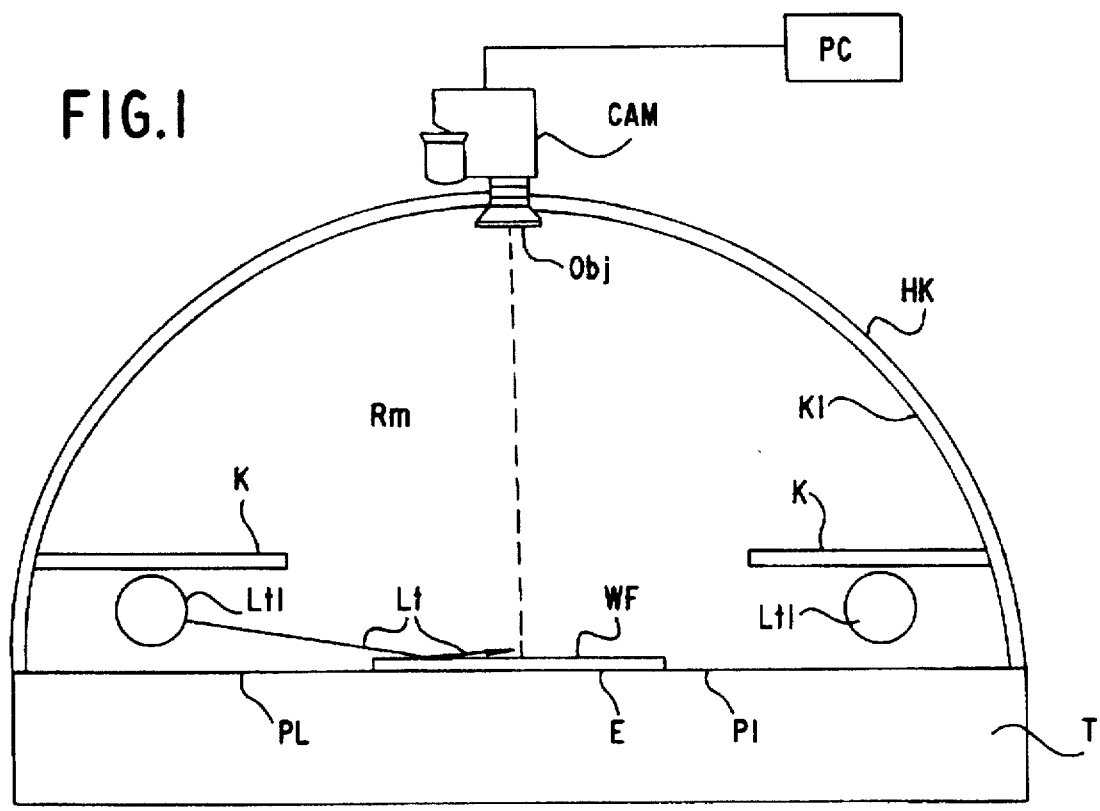
FIGS. 1–3 are diagrammatic, side-elevational views of advantageous embodiments of the apparatuses according to the invention that make the method possible.
Figure 2:
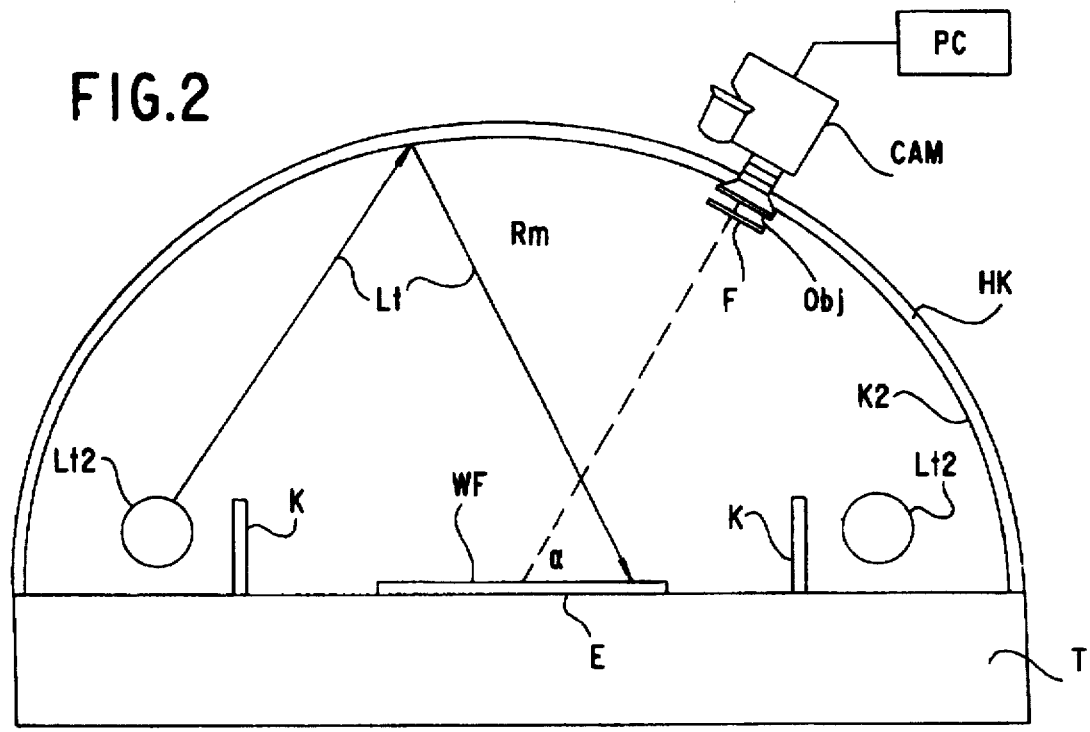
Figure 3:
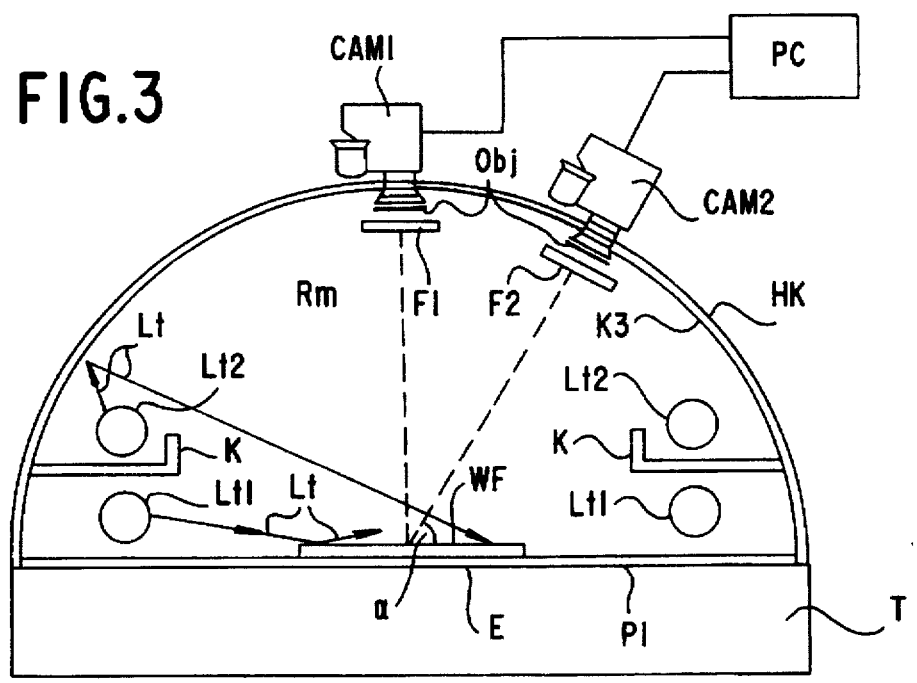

Referring now in detail to the figures of the drawing, with the aid of which a first embodiment of the apparatus according to the invention that is suitable for the method will be briefly described before the method of the invention is described in detail, and first, particularly, to FIG. 1 thereof, there is seen an apparatus which may be disposed on a table T, for example (the same is also true for the other two embodiments of FIGS. 2 and 3), or on some other suitable support that stands firmly. The apparatus has a receiver or device E for receiving a semiconductor wafer WF to be checked, and a bottom plate P1. However, the bottom plate P1 is not absolutely necessary. The device E may be a component of the bottom plate P1. However, in other embodiments of the apparatus according to the invention, it may alternatively be disposed on or let into the bottom plate P1. The apparatus also has a hemispherical hood device or hood HK, which forms a largely closed interior Rm with the bottom plate P1, and which has a surface K1 in the interior Rm that largely absorbs any incident light Lt and is optionally black.

Inside this interior Rm is a preferably but not absolutely necessarily annular lighting device or light Lt1, which serves to provide direct illumination of the semiconductor wafer WF. The annular embodiment enables uniform illumination of the semiconductor wafer WF. Inside the closed-off space Rm, the hemispherical hood device HK has a surface K1, which absorbs incident light Lt.

Disposed above the lighting device Lt1 is a further hood device or hood K, which does not admit, and as much as possible absorbs, incident light Lt. It is constructed in such a way that the semiconductor wafer WF can be illuminated directly by the lighting device Lt1, while the hemispherical hood HK is for the most part shielded from the direct light of the lighting device Lt1. Due to these requirements, it is advantageous, especially if there is an annular construction of the lighting device Lt1 for the further hood device K to be annular as well.

A camera CAM is disposed vertically above the center point of the device E for receiving the wafer WF to be checked. The camera CAM is disposed on the hemispherical hood device HK in such a way that its lens Obj looks into the closed-off space or interior Rm, particularly at the point 'where the semiconductor wafer WF to be checked is located during operation. The camera CAM may be disposed in such a way that its lens Obj protrudes into the closed-off space Rm, as is shown in FIG. 1, or else in such a way that the edge of its lens Obj is approximately flush with the hemispherical hood HK.

The camera CAM is connected to an evaluation device PC, which serves to control the camera and to receive, buffer-store, process and output data transmitted from the camera CAM. These data may be transmitted in analog form (in the form of "pictures") or in digital form, if the camera CAM is already equipped for digital transmission (for instance, if it has A/D converters). The evaluation device PC is typically a computer, for instance a personal computer or a data processing system. However, it is also conceivable for it to be constructed solely with hardware that executes the method to be described below.

The following features of the apparatus are advantageous:

The surface K1 of the hemispherical hood HK that absorbs the light Lt is black.

The light Lt output by the lighting device Lt1 is white.

The further hood device K has a black surface.

The surface of the bottom plate P1 is black on its side facing toward the hemispherical hood device HK.

If other parts of the camera CAM are located inside the closed-off space Rm, then they are disposed in such a way that they are concealed by the lens Obj, as seen from the standpoint of the semiconductor wafer WF to be checked.

The method which is described below in conjunction with FIGS. 4-8 can be carried out through the use of this apparatus and optionally its advantageous further refinements. It is suitable both for checking individual semiconductor wafers WF and for checking from a plurality of the semiconductor wafers WF to all of the semiconductor wafers WF in a batch of semiconductor wafers WF (that is, semiconductor wafers WF which are part of a common production lot). In the case in which semiconductor wafers WF in a batch are checked, certain method steps are only absolutely necessary for the first semiconductor wafer WF of this batch. The results of these certain method steps, given suitable buffer storage by means of the evaluation device PC, can be further used to check the other semiconductor wafers WF of the applicable batch. These method steps, which are absolutely necessary only for the first semiconductor wafer WF of a batch, are also disclosed below.

Figure 5:
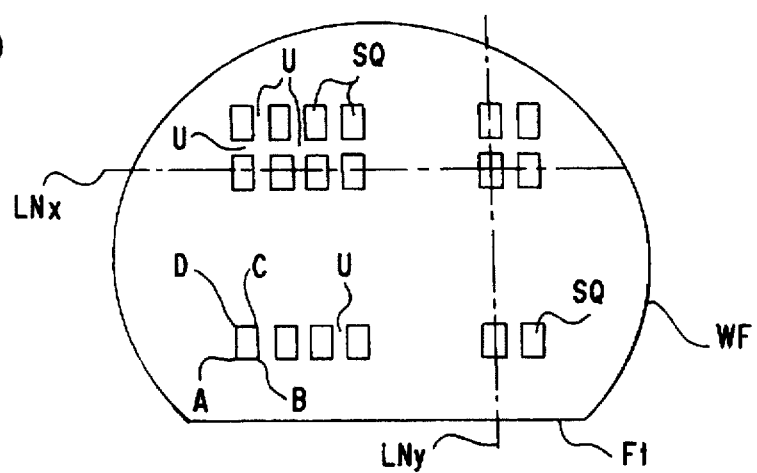
FIG. 5 is a side-elevational view of a wafer with a flat region.

Since semiconductor wafers WF often have a so-called flat Ft (that is, a region on the intrinsically round semiconductor wafer WF is flattened) as is seen in FIG. 5, the assumption in the ensuing method will be that the semiconductor wafers WF to be checked have such a flat Ft. However, the semiconductor wafers WF could instead have a notch, although in principle this has no effect on the method. Even semiconductor wafers WF without such aids in orientation can be checked by means of the method, for instance if image processing programs are used that can ascertain the orientation of rectangular surfaces of regular structures SQ to be described below. It is also assumed that the semiconductor chips to be formed on the semiconductor wafers WF in the manufacturing process are rectangular, optionally square, and are aligned parallel to the flat Ft. Although the method of the invention is also applicable to semiconductor wafers WF that do not meet these prerequisites, nevertheless in that case additional positioning steps are needed to align the semiconductor wafer WF into a position which is common to all of the wafers and/or to recalculate positions of the individual chips to be made on the semiconductor wafer WF, although this requires no inventive activity, in comparison with the teaching of the invention.

It is assumed as well that the semiconductor chips to be made from the semiconductor wafer WF to be checked are integrated semiconductor memories which, regardless of their memory type (volatile memories such as DRAMs, SRAMs, and nonvolatile memories [NV memories] such as ROMs, PROMs, EEPROMs), are known to have large regions SQ of regular structures (so-called memory cell blocks or memory cell fields), as is seen in FIG. 5, as well as regions of irregular structures which, for instance, contain so-called peripheral circuits, such as decoders and amplifiers, and connection surfaces (pads). The regions of regular structures SQ as a rule make up from 80 to 95% of the total memory chip. On such a semiconductor wafer WF, there are also regions (generally called scored frames) between the individual chips that are used to break apart the (finished) semiconductor wafer WF into a chip card or the like for the mounting of the individual chips in a housing. In the method according to the invention, only those regions of regular structures SQ are checked. In view of their large proportion of the entire surface area of the semiconductor wafer WF, this is entirely adequate.

Another prerequisite of the method according to the invention is that the semiconductor wafer WF (shown in FIG. 4) have at least one layer that already contains structures St of the semiconductor chips to be completed, as well as a lacquer layer L (for additional structuring steps) as the top layer, and these layers need to be checked.

One essential characteristic of the method of the invention is that the check proceeds automatically, or in other words without the intervention of human activities. On one hand, this protects the health of workers (see the disadvantages of the prior art discussed above). On the other hand, it also promotes the accuracy of the check, for the following reasons:

More measurement points can be checked in the same or even less measuring time (per wafer), that is the checking is more accurate.

Human mistakes (transposing the detection of good/reject and sorting in accordance with good/reject) are precluded.

At a short measuring time per wafer, the throughput, in other words the productivity per employee, increases.

The method of the invention moreover offers the possibility of having one employee handle and/or check a plurality of apparatuses according to the invention that carry out the method (such as setting the wafers down and taking them away again, if this has not been automated, and starting the method, if this has not been automated), so that the productivity can be increased even further (higher productivity is well known to mean lower manufacturing costs, which is eminently important today for manufacturers of integrated circuits, and especially manufacturers of integrated semiconductor memories).

The method of the invention is carried out in such a way that for at least the first semiconductor wafer WF of a batch (or, it is understood, possibly also with others of this batch or even all of the remaining semiconductor wafers WF of this batch) the following events proceed or are carried out:

The semiconductor wafer WF is illuminated directly by the lighting device Lt1, for instance with white light. The lacquer layer L applied to the semiconductor wafer WF reflects the light Lt.

Through the use of the camera CAM, which is disposed vertically above the semiconductor wafer WF and which "looks" at the semiconductor wafer because of this configuration, the degree of reflection, or reflectance, R of the reflected light Lt will be ascertained as follows (reflectance R is understood in this case to mean the measure of brightness, from the semiconductor wafer WF which strikes or acts upon the lens of the camera CAM):

First, through the use of the evaluation device PC, a first line LNx, which serves as a measurement line and extends parallel to and at a given distance from the flat Ft, is simulated, or in other words "imagined", on the surface of the lacquer L of the semiconductor wafer WF, as is seen in FIG. 5. The brightness of the semiconductor wafer WF, that is the value of the reflectance R, is ascertained by the camera CAM and the evaluation device PC along this imaginary line LNx at selected points Px ("pixels", which are not shown for the sake of simplicity) and buffer-stored together with a position value x of these points Px, in the evaluation device PC.

Figure 6:
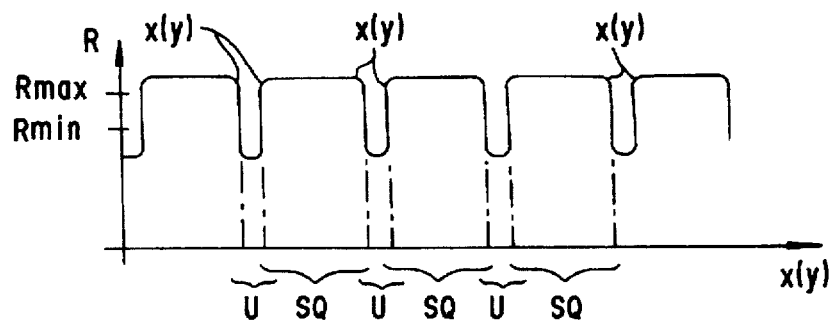
FIG. 6 is a diagram showing measured values of reflectance.

Referring to FIG. 6, if values for the ascertained and measured reflectance R that are below a predetermined minimum value Rmin are found along this imaginary line LNx multiple times, then the ascertained and buffer-stored delta referring to this line LNx are discarded as unusable. It is assumed in fact that the line LNx does not extend predominantly through the large surfaces of the regular structures SQ of the regular structures but rather through the regions of irregular structures or through a scored frame. However, these regions and the scored frame (known as the "U" seen in FIG. 5) are not to be checked, by agreement. Instead of the imaginary line LNx which has been surveyed, a further "imaginary" line LNx1 is selected at a given distance from the imaginary line LNx and used (this is not shown in FIG. 5 for the sake of simplicity), and the reflectance R is also ascertained and buffer-stored with respect to the line LNx1, along with the associated position values x, as was done for the originally used imaginary line LNx.

If the values of the reflectance R of this further imaginary line LNx1 also have values below the minimum value Rmin multiple times, then the entire process of "discarding the data of this line LNx1, assumption of a further imaginary line LNx2, ascertainment and evaluation of the values of its reflectance R and of the associated position values x, and buffer-storing" is carried out once again as described above.

This is done overall often enough until an imaginary line LNx, LNx1, LNx2, . . . has been found having values for the reflectance R which meet the criterion of the minimum value Rmin multiple times. If no such imaginary line LNx, LNx1, . . . can be ascertained (optionally limited to a maximum number of attempts to find a suitable line LNx) that meets this criterion, then the check of this semiconductor wafer WF is discontinued, because it is assumed that either a defect of greater extent is involved, or the semiconductor wafer WF perhaps does not even have any structures St underneath the lacquer layer L.

In the case in which the search for an imaginary line LNx, . . . that is located parallel to the flat Ft has lead to values for the reflectance R that meet the criterion of the minimum reflectance Rmin multiple times, then completely an accordance with the previous line, a new imaginary line LNy is simulated, somewhere over the semiconductor wafer WF to be checked, at right angles to the imaginary line that was found (it will be assumed below that this line which was found was the first imaginary line LNx), as is seen in FIG. 5. The values of the reflectance R of the reflected light Lt (together with the associated position values y) are again measured along this new imaginary line, at measurement points Py, by means of the camera and are buffer stored in the evaluation device PC. These values must again meet the criterion of the minimum reflectance Rmin multiple times (although it is conceivable that this reflectance may have a different value than for the imaginary line LNx parallel to the flat Ft). If the values do not meet that criterion, then the steps already described for the imaginary line LNx for finding an imaginary line LNx1, LNx2, . . . are carried out analogously with respect to the new imaginary line LNy, with additional new imaginary lines LNy1, LNy2, etc. (each time at a given distance from the previously measured new imaginary line LNy, LNy1, etc.), until such time as it is either found (optionally after a predetermined maximum number of attempts) that no new imaginary line LNy, . . . can be found which meets the criterion of the minimum reflectance Rmin (in which case checking of the affected semiconductor wafer WF is discontinued), or until such a line has been found (this will be assumed, for the purposes of the further description below, to be the original line LNy).

In the event that it has been possible to find a usable imaginary line LNx and LNy, then the position values x (for the imaginary line LNx) and y (for the imaginary line LNy) at the various measurement points of these lines LNx and LNy are already in buffer storage. The position values are referred to the location of the flats Ft. If at all possible, the measurement points Px and Py should be spaced so closely together that the boundaries between the various spaces of the regular structures SQ and the regions U (irregular structures and scored frames) are detected as accurately as possible (for instance, by way of their associated values for the reflectance R).

FIG. 6 shows an example of the course of the measured values of the reflectance R along the imaginary line LNx. The same is correspondingly true for the imaginary line LNy, as given by the letter "y" in parentheses on the abscissa. In the diagram, "SQ" stands for the (presumably rectangular) large surfaces of regular structures SQ, while "U" stands for the (smaller) regions of irregular structures and the various scored frames. The other designations "X", "Y" (in parentheses) that are also used will be explained later below. The drawing is based on the fact that the large surfaces of the regular structures SQ in the normal case have high values of the reflectance R, while the regions U have a usually markedly lower value for the reflectance R.

Figure 7:
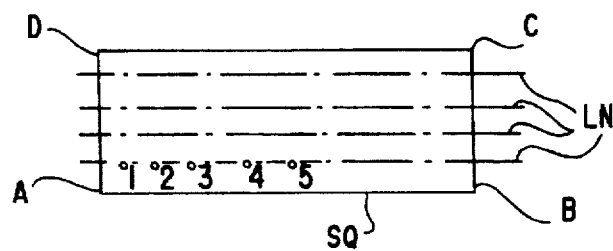
FIG. 7 is an enlarged view of a wafer having measuring lines.

In the case of the further method steps, that is for a semiconductor wafer WF for which imaginary lines LNx, LNy had been found that met the criterion of the minimum value Rmin, those points or in other words coordinates X, Y (see FIG. 6) that are of interest are those that are located at the periphery of the large surfaces of the regular structures SQ and the other regions U of irregular structures and the scored frames (that is, corner points A, B, C, D of the large surfaces of the regular structures SQ, as is shown in FIGS. 5 and 7), since the regions U are to be precluded from the check, by agreement. To that end, these coordinates X, Y are ascertained by means of the evaluation device PC from the position points x of one imaginary line LNx (or the further imaginary line LNx1 or LNx2, etc. being used as a substitute for it) and the position points y of the other imaginary line LNy (or the further imaginary line LNy1 or LNy2, etc. being used as a substitute for it) having associated values of the reflectance R, and the information that the surfaces of the regular structures SQ (that is, the memory cell fields) are rectangular.

The ascertainment is performed in a way which is easily carried out mathematically from the information that the large surfaces of the regular structures SQ form rectangles which repeat regularly in the x and y directions (that is, parallel and vertically to the flat Ft and thus parallel and vertically to the respective imaginary lines LNx, LNy) and from the evaluation criterion that only those position points x and y of the two imaginary lines LNx, LNy having an associated value of the reflectance R which exceeds a predetermined maximum value Rmax, that at the same time are neighboring points of position values x and y which fall below this maximum value Rmax, are taken into account. All of the position points x and y having an associated value of the reflectance R which is below this maximum value Rmax are considered to be regions U that are not to be checked and are thus ignored in the remainder of the method.

Thus, with respect to the semiconductor wafer WF to be checked, all of the rectangular surfaces of the regular structures SQ (which may optionally be square, as a special case of a rectangle) within which the check is to be performed are defined. The regions U are by agreement precluded from the check. Incomplete surfaces of the regular structures SQ, which correspond to the incomplete peripheral chips of a semiconductor wafer WF, can also be precluded from the check.

Since the geometric configuration of the surfaces of the regular structures SQ and the regions U for all of the semiconductor wafers WF of a batch are the same with respect to the flats Ft thereof (because they are jointly manufactured), the coordinates X, Y of the surfaces of the regular structures SQ, which have been ascertained and buffer-stored by the above-described method steps, may (but need not) also be employed for the other semiconductor wafers WF of the same batch, given a suitable orientation of these wafers on the device E, so that the above-described method steps can be omitted in checking the further semiconductor wafers WF of the same batch. This economizes on computer time.

The further method steps, which will be described below for a surface of the regular structures SQ, are employed successively on each individual rectangular surface of the regular structures SQ of the semiconductor wafer WF. They are again based on the principle of imaginary lines, but unlike the imaginary lines LNx, LNy described above they will now be referred to as measuring lines LN.

In the case of each of the rectangular surfaces of the regular structures SQ to be checked, as is seen in FIG. 7, at least one measuring line LN is "drawn by imagination" parallel to one edge (four measuring lines LN that are parallel to the respective edges AB and CD are shown in FIG. 7 by way of example). Although this preferably takes place parallel to the longer edge of the surface of the regular structures SQ, it may also be parallel to the shorter edge.

Along each of these measuring lines LN, the applicable value of the reflectance R is ascertained by means of the camera CAM and the evaluation device PC and buffer-stored for predetermined measurement points 1, 2, 3, . . . . The more measuring lines LN that are used per surface of the regular structures SQ and the more such points 1, 2, 3, . . . that are given, the more accurate the checking becomes.

Figure 8:
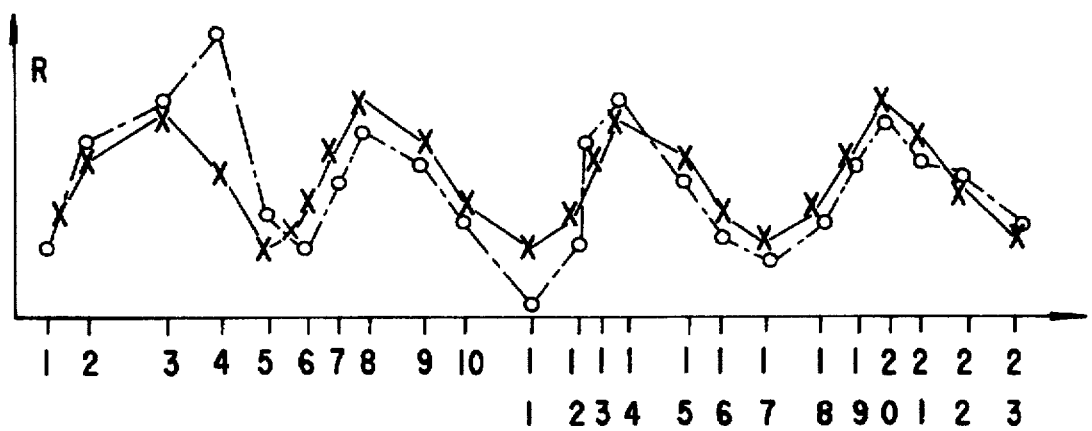
FIG. 8 is a diagram showing courses of the reflectance.
Figure 4:
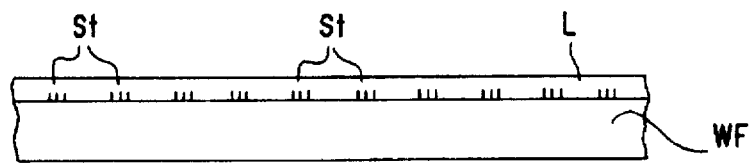
FIG. 4 is a fragmentary, side-elevational view of a wafer having structures and a lacquer layer.

In the case of the reflectance R along two selected measuring lines LN, the two courses shown in FIG. 8 (which need not necessarily be a kind of sinusoidal curve) result, for example. The measurement points 1 to 23 are plotted on the abscissa. The applicable value of the reflectance R can be read off from the ordinate.

The values marked "x" of the reflectance R are values along a first measuring line LN. As the possible criteria to be described below for detecting whether or not a defect is present indicate, no defect can be found along this measuring line. Although various values of the reflectance R are present (caused by the various structures inside the surface of the regular structures SQ, under the lacquer layer L), nevertheless, as can be seen from the evaluation criteria given below, these values are within the range of the usual values to be expected, so that the surface of the regular structures SQ being checked with reference to this measuring line LN can be judged "good". The values of the reflectance R exhibit a periodic course. This is due to the fact that modern integrated semiconductors (one of which is of course to be made along with the present semiconductor wafer WF, and therefore by means of the surfaces of the regular structures SQ in question) have a plurality of memory cell fields disposed next to one another. Each period shown is accordingly equivalent to one such (future) memory cell field.

The values marked "o" for the reflectance R in FIG. 8 are measurement values along a second measuring line LN, for instance of the same surface of the regular structures SQ. The measurement points 4 and 11 are particularly striking.

The value of the reflectance R for the measurement point 4 (that is, within the first period) is markedly above the other measurement points, and especially with respect to the local maximum values thereof within each of the further periods 2, . . . . A defect is involved in this case, which is caused by a white particle. Since a white particle better reflects the light Lt than the other points of the lacquer layer L, this value is especially high.

The value of the reflectance R at the measurement point 11, which (coincidentally) is located at the transition from the second to the third period, is especially low as compared with the other measurement points, and especially as compared with the minimum values of the various periods. This can be ascribed to the fact that a dark particle is present at the affected point of the surface of the regular structures SQ, which is located between the second and third (yet to be made) memory cell field. However, it could also be that at this point the lacquer layer L is too thin or even has a hole in it. Thus, in the further production of the memory chip, structuring defects such as underetching, etc., could occur at this point. In any case, the measured values along the second measuring line LN indicate two defects, each individual one of which, upon being detected, causes the semiconductor wafer WF to be accordingly shunted elsewhere and possibly reworked.

With the aid of the measurement points 1, 2, . . . per measuring line LN, the evaluation device PC accordingly ascertains from evaluation criteria whether the rectangular surface of the regular structures SQ, and thus the entire semiconductor wafer WF being investigated, is OK or is defective. The results (optionally along with the geometrical data of where defects are located) can then be output by the evaluation device PC, for instance in the form of data on storage media (magnetic tapes, hard disk), by printout, or by triggering appropriate machines for post processing. Many kinds of possibilities are conceivable in this case.

The following evaluation criteria in particular can be used in determining whether the semiconductor wafer WF being checked, or its rectangular surfaces of the regular structures SQ, are or are not OK:

Either for each separate measuring line LN of a surface of the regular structures SQ, or for all of the measuring lines LN of the affected surface of the regular structures SQ, the maximum values of reflectance R of the individual periods that occur can be ascertained and thereupon checked as to whether or not they differ from one another by more than one predetermined allowable differential value. If so, a defect is assumed and the applicable value and the associated coordinates are buffer-stored and optionally output or further processed.

The same can be done for the corresponding minimal values of the reflectance R. The following can be carried out as a further evaluation criterion: Through the use of the evaluation device PC, a mean value is formed with respect to the surface of the regular structures SQ being checked, from all of the values ascertained for the reflectors R, either along a single measuring line LN or along all of the measuring lines LN. Any deviation of this mean value by more than a predetermined amount from a predetermined value is considered to indicate a defect. A corresponding averaging with respect to the periodically occurring maximum values (or the minimum values as well) of the reflectance R in combination with a comparison with a correspondingly predetermined value and looking for any deviation of this value by more than a predetermined amount, is again an advantageous evaluation criterion.

These evaluation criteria are each usable alone in carrying out the method of the invention. However, they can also be combined in part or completely with one another.

In the case in which another rectangular surface of the regular structures SQ of the same semiconductor wafer WF had already been checked before the surface of the regular structures SQ currently to be checked, the following evaluation criterion can also be employed: one, more than one, or all of the values of the reflectance R of the measuring lines LN of the current surface of the regular structures SQ are compared with the corresponding values of the corresponding measuring lines LN of the surface of the regular structures SQ tat were checked previously. A deviation of the various pairs of values from one another by more than a predetermined differential amount then helps to make the decision as to whether or not a defect is involved.

Instead of the comparison of the various values of the reflectance R, as just described, other evaluation criteria may be used as follows: a comparison of the corresponding maximum values with one another or of the corresponding mean values of these maximum values with one another; a comparison of the corresponding minimum values with one another, or of the various mean values of these minimum values with one another; and a comparison of the various mean values of the measured values with one another. A particular predetermined differential amount, which if it is exceeded indicates a defect, is then used to decide whether a defect is present or not.

Once all of the rectangular surfaces of the regular structures SQ of the semiconductor wafer WF have then been checked by the means described above and corresponding statements have been made about the wafer WF being checked, then the first embodiment of the method of the invention is at an end. However, in a special embodiment of the invention it is possible to employ basic traits of this method once again under different conditions, particularly for the surfaces of the regular structures SQ of the semiconductor wafer WF that have previously been found good, by using a different apparatus for carrying out this method. In the process, those method steps that serve to detect and identify the rectangular surfaces of the regular structures SQ to be checked and the regions U to be omitted from the check can be repeated.

However, they may also be omitted if the coordinates X, Y of the surfaces of the regular structures SQ to be checked have been adopted from the method described above and if suitable adjustment of the semiconductor wafer WF with its flat Ft relative to the device E is performed, since the coordinates X, Y are stored in memory relative to the flat Ft in the evaluation device PC. First, the apparatus required for this new performance of the method will be described, in conjunction with FIG. 2.

This apparatus is constructed similarly to the first embodiment but differs markedly from it in some points.

It too has a device E for receiving the semiconductor wafer WF to be checked, and an illuminating device or light Lt2. However, the latter serves to illuminate the semiconductor wafer WF indirectly. The hemispherical hood device HK that was already described is also present, but with a surface K2 in its interior that to a great extent reflects incident light Lt. It is therefore preferably white. A further hood device K that absorbs incident light Lt is also disposed between the lighting device Lt2 and the device E for receiving the semiconductor wafer WF to be checked, and this hood device is constructed in such a way that it prevents light from directly striking the device E and the semiconductor wafer WF. In other words, the semiconductor wafer WF can only be lighted indirectly with the lighting device Lt2, by reflection of the light Lt at the hemispherical hood device HK. A camera CAM is again disposed on the hemispherical hood HK in such a way that its lens Obj looks into the space Rm inside the hemispherical hood device HK. However, the camera cam is not disposed vertically as in the first embodiment of FIG. 1 with respect to the center point of the device E for receiving the semiconductor wafer WF, but rather at an angle α that is greater than 0 and less than 90°. An angular position of from 40° to 70° has proved good, with an optimal value being 60°. In this case, the camera can in fact reflect neither directly nor indirectly onto the semiconductor wafer WF, which would impede detection of the values of the reflectance R. It is also advantageous if the lens Obj of the camera CAM is equipped with a red filter F, which increases the contrast of the picture being taken.

The camera CAM, as in the first embodiment, is connected to an evaluation device PC, which serves to control the camera CAM and to receive, process, buffer-store and output the data or images transmitted by the camera CAM.

The following further features are advantageous in both embodiments of the apparatus (that is, in the apparatuses of FIGS. 1 and 2):

The light of the lighting devices Lt1 and Lt2 is white. The further hood devices K have a black surface. Further parts of the camera CAM, if any, which are located inside the hemispherical hood device HK, are disposed in such a way that they are concealed by the lens Obj when observed from the semiconductor wafer WF or the device E. It is also advantageous, for the sake of uniform illumination, if the lighting devices Lt1 and Lt2 and/or the further hoods K are annular. A bottom plate P1 is not absolutely necessary (except perhaps for mechanical reasons, reasons of stability, or for the sake of simpler processing of pictures being taken). However, if it is present, then it should be light-absorbent, and preferably black.

With the thus-modified second apparatus, the following method can then be appended to the method described above:

The semiconductor wafer WF (to be checked in a second path) is indirectly illuminated by means of the lighting device Lt2 and the hemispherical hood device HK with its reflective surface K2. Due to the camera CAM disposed at the angle α, the rectangular surfaces of the regular structures SQ are now distorted in their coordinates X1, Y1 as compared with the first configuration. The distortions are calculated by the evaluation device PC from the angle α of the camera position and from the original coordinates X, Y. With the aid of these calculated, distorted coordinates X1, Y1 for each surface of the regular structures SQ, the method described at the outset is then performed again with respect to the checking of the rectangular surfaces of the regular structures SQ itself (that is, not the first steps, which involve ascertaining the surfaces of the regular structures SQ and their coordinates X, Y). The same evaluation criteria as already described above may be employed.

It is advantageous, because it saves on computer time and thus shortens the work, if this modified method is employed with an obliquely positioned camera CAM only for those surfaces of the regular structures SQ that were found to be good in the method described at the outset, with the camera in the vertical position.

Although this further method also takes time, nevertheless this embodiment has the following essential advantage: defects occur in and/or under the lacquer layer L that cannot be rendered visible and thus are detectable with a vertically positioned camera CAM and/or with direct illumination of the semiconductor wafer WF. However, with this further method, that is by means of indirect lighting and an obliquely placed camera CAM, even those defects can be detected in most cases, so that reworking of the affected semiconductor wafers WF can be performed in good time, which in turn increases the yield of semiconductor memories to be made and therefore lowers overall production costs.

A third embodiment of the apparatus for carrying out the method makes it possible to perform all of the above-described method steps, in other words both those in which the camera CAM is vertical and those in which the camera CAM is disposed obliquely at an angle α, by means of a single apparatus, namely that of the third embodiment. This apparatus will now be described in conjunction with FIG. 3.

Once again, the apparatus has a device E for receiving the semiconductor wafer WF to be checked. It has two lighting devices Lt1, Lt2, of which the first lighting device Lt1 serves to provide direct lighting of the semiconductor wafer WF with a first color Gn, that is preferably green, and the second lighting device Lt2 serves to provide indirect lighting of the semiconductor wafer WF, with a second color Rt, which is complementary to the first color Gn. The second color Rt is preferably red. A hemispherical hood device HK, which is once again a component of this third apparatus, has a surface K3 that is likewise of the second color Rt or in other words preferably red, in its interior Rm. Through the use of a bottom plate P1 which is only optionally present in this embodiment, the hemispherical hood HK forms a largely closed interior Rm. This bottom plate P1 may have the second color Rt, that is, preferably red, on its surface facing toward the space or interior Rm. However, in accordance with another feature, the surface may also be black. Above the first lighting device Lt1 is a further hood device K, which is opaque to incident light Lt. The further hood device K is advantageous if the hood device K is light-absorbent. The further hood device K is constructed in such a way that on one hand the semiconductor wafer WF can be lighted directly by means of the first lighting device Lt1, and on the other hand this semiconductor wafer WF can only be lighted indirectly by the second lighting device Lt2.

A first camera CAM1 is disposed on the hemispherical hood device HK vertically above the center point of the device E for receiving the semiconductor wafer WF. The first camera CAM1 is disposed in such a way that its lens Obj protrudes into the interior Rm inside the hemispherical hood device HK, and in that space looks at the device E. The first camera CAM1 has a filter F1, which admits only light of the first color Gn, or in other words preferably green light (that is, it is a green filter).

A camera CAM2 is also disposed on the hemispherical hood device HK in such a way that its lens Obj looks into the space Rm inside the hemispherical hood device HK and looks in the space at the device E. The second camera CAM2 also has a filter F2, but it admits only light of the second color Rt, that is preferably red light (in other words, it is a red filter).

The second camera CAM 2 is disposed at an angle α relative to the center point of the device E that is larger than 0° and at maximum is large enough to ensure that the second camera CAM2 does not come into contact with the first camera CAM1.

Both cameras CAM2, CAM2 are connected to an evaluation device PC, which serves to control the camera CAM1, CAM2 as well as to detect, buffer-store, further process and output data or images obtained from the cameras CAM1, CAM2.

This third embodiment of the apparatus can now be used as follows, by employing the method of the invention:

In the case of the first method steps, which are used to recognize and detect the individual rectangular surfaces of the regular structures SQ along with their coordinates X, Y, and the second method steps, which are used for the actual checking of the surfaces of the regular structures SQ and thus of the semiconductor wafers WF by means of a vertical camera (CAM in the first embodiment of the apparatus), the semiconductor wafers WF to be checked are checked by means of the first lighting device Lt1 and the first, vertical camera CAM1 in the manner already described above.

Next, for the method steps described last above, which have been described in terms of the second embodiment of the apparatus (or in other words which are carried out by indirect illumination of the semiconductor wafers WF and with the obliquely positioned camera CAM), the first lighting device Lt1 and the first camera CAM1 are turned off, and instead, the method is carried out by means of indirect lighting (that is, the lighting is provided by the second lighting device Lt2) and the second, obliquely positioned camera CAM2, in accordance with the method step described above in terms of the second embodiment of the apparatus.

In order to ensure that the two different types of lighting (direct and indirect lighting) with their light conditions, including reflections that occur or that are to be suppressed, will influence one another as little as possible at the hemispherical hood device HK, the system has been chosen to have the mutually complementary colors Gn, Rt of the lighting devices Lt1, Lt2 and the correspondingly constructed surfaces of both the hood device HK and optionally the bottom plate P1.

It is also advantageous if parts of the cameras CAM1 and/or CAM2 located in the space Rm inside the hemispherical hood device HK, for one of the two cameras CAM1, CAM2 or both cameras CAM1, CAM2, are disposed in such a way that they are concealed by the lens Obj of the respective camera CAM1, CAM2, as viewed from the semiconductor wafer WF or from the device E.

It is additionally advantageous if at least one of the two lighting devices Lt1, Lt2 and/or the further hood device K is annular or is disposed annularly.

The device E for receiving the semiconductor wafers WF may also be advantageously constructed in various ways: it may be constructed as a component of the bottom plate P1, it may be disposed on the bottom plate P1, or it may be let into the bottom plate P1.

It is likewise advantageous (in terms of the second apparatus) if the angle α, at which the second camera CAM2 is disposed relative to the center point of the device E, is from 40° to 70°. A configuration of 60° is optimal.

We claim:

1. In a method for checking semiconductor wafers or a batch of semiconductor wafers used to produce integrated semiconductor memories, in which the semiconductor wafers have a lacquer layer and at least one layer having structures below the lacquer layer, the improvement which comprises automatically:

1) ascertaining regions to be omitted from the check and surfaces to be checked, at least for first semiconductor wafers to be checked, in accordance with the following steps:
   1a) directly illuminating the semiconductor wafer for reflecting light from the applied lacquer layer;
   1b) ascertaining and buffer-storing reflectance of the reflected light with a camera disposed vertically above the semiconductor wafer and an evaluator connected to the camera, in the following way:
      1b1) ascertaining and buffer-storing the reflectance of the reflected light at selected points along two imaginary lines drawn over the semiconductor wafer at right angles to one another, with one of the lines being aimed in a forward direction of the structures;
      1b2) repeating step 1b1) for a further imaginary lines being spaced apart from and parallel to the imaginary line and having multiple values below a predetermined minimum value, if multiple values for the reflectance being below the minimum value occur for at least one of the imaginary lines;
      1b3) repeating step 1b2) with further imaginary lines being spaced apart from the last imaginary line measured most recently, if step 1b2) for the further imaginary line also leads to values of the reflectance being below the minimum value multiple times, often enough until an imaginary line is found having values of the reflectance meeting the criterion of the minimum value multiple times;
   1c) discontinuing the check if steps 1b1) through 1b3) do not lead to two imaginary lines at right angles to one another meeting the criterion of the minimum value; otherwise ascertaining coordinates being above a predetermined maximum value but in the vicinity of position values having a reflectance below the maximum value for each of the two imaginary lines, from their position points, from associated values of the reflectance and from information stating that the semiconductor wafer serves to produce integrated semiconductor memories;
   1d) utilizing a quantity of the coordinates thus found in a remainder of the method to eliminate regions of the semiconductor wafer to be checked, from the check, for finding a number of surfaces to be checked for the semiconductor wafer to be checked, having coordinates of corner points being equal to the ascertained respective coordinates;

2) checking each surface during illumination, by the following method steps:
   2a) drawing at least one imaginary measuring line through the surface to be checked;
   2b) ascertaining and buffer-storing a respective value of the reflectance of the reflected light at predetermined measuring points along the measuring line with the camera and the evaluator;
   2c) ascertaining whether the checked surface is OK or defective in accordance with at least one predetermined evaluation criterion, from the ascertained and buffer-stored values of the reflectance; and
   2d) ascertaining surfaces found to be defective.

2. The method according to claim 1, which comprises making the corresponding coordinates ascertained for a first wafer of a batch the basis of the check of the surfaces of a current semiconductor wafer, for a second and further semiconductor wafers of the same batch of semiconductor wafers, instead of ascertaining the coordinates of the corner points of their surfaces by steps 1) through 1d).

3. The method according to claim 1, which comprises:
   illuminating the semiconductor wafer indirectly;
   placing the camera at an angle of greater than 0° and less than 90° relative to the surface of the semiconductor wafer;
   calculating distortions with respect to the coordinates of the surfaces resulting from the placement of the camera, from the originally ascertained coordinates of the surfaces and the selected angle of the camera; and
   carrying out steps of 2) through 2d) on the basis of the calculated coordinates.

4. The method according to claim 3, which comprises performing a check with the camera disposed at the angle, only for the surfaces that have been found to be OK in the check performed with the vertically positioned camera.

5. The method according to claim 1, which comprises using periodically occurring maximum values of the reflectance as an evaluation criterion for the surface to be checked, and evaluating a deviation of the maximum values from one another by more than a predetermined differential value as being defective with respect to the surface to be checked.

6. The method according to claim 5, which comprises comparing at least some of the ascertained values of the reflectance for the surface to be checked with a corresponding group of various ascertained values of the surface that was already checked before the surface currently to be checked, using a deviation of the thus-compared values by a predetermined differential amount as an evaluation criterion; and using a deviation of the respective maximum values by more than a predetermined amount from one another as the evaluation criterion for the surface to be checked, instead of the ascertained values of the reflectance of that surface and of the surface that was checked before that surface.

7. The method according to claim 1, which comprises forming a mean value from all of the ascertained values of the reflectance along at least one of the measuring lines of a surface, and using a deviation of the mean value by more than a predetermined amount from a predetermined value as an evaluation criterion for the checked surface.

8. The method according to claim 7, which comprises comparing at least some of the ascertained values of the reflectance for the surface to be checked with a corresponding group of various ascertained values of the surface that was already checked before the surface currently to be checked, using a deviation of the thus-compared values by a predetermined differential amount as an evaluation criterion; and using a deviation of the mean values of the various values of the reflectance from one another by more than a predetermined amount as the evaluation criterion for the surface to be checked, instead of the ascertained values of the reflectance of that surface and of the surface that was checked before that surface.

9. The method according to claim 1, which comprises forming a mean value from the periodically occurring maximum values of the reflectance along at least one of the measuring lines of a surface, and using a deviation of the mean value by more than a predetermined amount from a predetermined value as an evaluation criterion for the checked surface.

10. The method according to claim 9, which comprises comparing at least some of the ascertained values of the reflectance for the surface to be checked with a corresponding group of various ascertained values of the surface that was already checked before the surface currently to be checked, using a deviation of the thus-compared values by a predetermined differential amount as an evaluation criterion; and using a deviation of the mean values formed from the respective periodically occurring maximum values or minimum values from one another by more than a predetermined amount as the evaluation criterion for the surface to be checked, instead of the ascertained values of the reflectance of that surface and of the surface that was checked before that surface.

11. The method according to claim 1, which comprises using periodically occurring minimum values of the reflectance as an evaluation criterion for the surface to be checked, and evaluating a deviation of the minimum values from one another by more than a predetermined differential value as being defective with respect to the surface to be checked.

12. The method according to claim 11, which comprises comparing at least some of the ascertained values of the reflectance for the surface to be checked with a corresponding group of various ascertained values of the surface that was already checked before the surface currently to be checked, using a deviation of the thus-compared values by a predetermined differential amount as an evaluation criterion; and using a deviation of the respective minimum values from one another by more than a predetermined amount as the evaluation criterion for the surface to be checked, instead of the ascertained values of the reflectance of that surface and of the surface that was checked before that surface.

13. The method according to claim 1, which comprises comparing at least some of the ascertained values of the reflectance for the surface to be checked with a corresponding group of various ascertained values of the surface that was already checked before the surface currently to be checked, and using a deviation of the thus-compared values by a predetermined differential amount as an evaluation criterion.

14. The method according to claim 1, which comprises drawing the imaginary measuring line parallel to the longer edge of the surface to be checked.

15. The method according to claim 1, which comprises drawing the imaginary measuring line parallel to the shorter edge of the surface to be checked.

16. The method according to claim 1, which comprises checking the surface to be checked through the use of more than one measuring line.

* * * * *